| United States Patent [19] | [11] Patent Number: 4,602,108 |
| McKinnie | [45] Date of Patent: Jul. 22, 1986 |

[54] ALKYL AMINE COLOR INHIBITOR

[75] Inventor: Bonnie G. McKinnie, Magnolia, Ark.

[73] Assignee: Ethyl Corporation, Richmond, Va.

[21] Appl. No.: 636,624

[22] Filed: Aug. 1, 1984

[51] Int. Cl.[4] .............................................. C07C 85/26
[52] U.S. Cl. ........................................ 564/2; 564/497
[58] Field of Search ............................................ 564/2

[56] References Cited

U.S. PATENT DOCUMENTS 2,637,636  6/1953  Walters .................................... 564/5
3,577,556  6/1971  Longoria ................................. 564/2

Primary Examiner—Charles F. Warren
Assistant Examiner—John A. Sopp
Attorney, Agent, or Firm—Donald L. Johnson; John F. Sieberth; Joseph D. Odenweller

[57] ABSTRACT

Color formation in aliphatic amines during storage is prevented by contacting the amines before they develop objectionable color with ethylenediamine tetraacetic acid, salts or ethylenediamine tetraacetic acid, nitrilotris acetic acid, salts of nitrilotris acetic acid, nitrilotris methylenephosphonic acid, salts of nitrilotris methylenephosphonic acid, 8-hydroxy-quinoline or mixtures of the above compounds.

6 Claims, No Drawings

ALKYL AMINE COLOR INHIBITOR

BACKGROUND OF THE INVENTION

Aliphatic amines find many uses in chemical industry. They are used as intermediates in the preparation of pharmaceuticals and organic dyes. They can be used as additives in petroleum products such as distillate fuel wherein they act as stabilizers. Aliphatic tertiary amines can be converted to quaternary ammonium salts which can be used to inhibit bacteria and fungus growth.

Several synthetic methods are available to make aliphatic amines. Fatty acids can be converted to amides and hydrogenated to form fatty amines. In another method, alpha-olefins are converted to alkyl bromides by reaction with HBr and then reacted with ammonia, alkyl amines or dialkyl amines to form useful aliphatic amines.

Initially, aliphatic amines made in commerce are substantially colorless. On storage especially when exposed to air they develop color which can be a problem in some markets. Most common antioxidants were found to be ineffective in preventing this color formation. Accordingly, a need exists for a method which will prevent color formation in aliphatic amines during storage.

SUMMARY

It has now been discovered that color formation in aliphatic amines can be prevented by contacting these amines with certain additives such as ethylenediamine tetraacetic acid (EDTA). The additives need not be soluble in the aliphatic amines and need only contact the aliphatic amines. Any insoluble additives can be readily removed from the aliphatic amine prior to use by conventional methods such as filtration.

DESCRIPTION OF THE PREFERRED EMBODIMENTS

A preferred embodiment of the invention is a color stabilized aliphatic amine composition comprising an aliphatic amine containing 1–50 carbon atoms and 1–6 amino nitrogen atoms and containing a color suppressing amount of an additive selected from the group consisting of ethylenediamine tetraacetic acid, salts of ethylenediamine tetraacetic acid, nitrilotris acetic acid, salts of nitrilotris acetic acid, nitrilotris methylenephosphonic acid, salts of nitrilotris methylenephosphonic acid, and 8-hydroxy-quinoline.

The present invention can be used to prevent or lessen color formation in any amine which tends to develop an objectionable color during storage especially when exposed to air. It is especially useful with aliphatic amines which includes aliphatic amines containing about 1–50 carbon atoms and about 1–6 amino nitrogen atoms. Examples of these amines are methyl amine, ethyl amine, n-butyl amine, isobutyl amine, n-octyl amine, 2-ethylhexyl amine, n-hexadecyl amine, 2-ethylhexadecyl amine, n-eicosyl amine, triacontyl amine, tetracontyl amine, pentacontyl amine, dimethyl amine, methyl ethyl amine, di-n-butyl amine, 2-ethylhexyl dodecyl amine, di-octadecyl amine, di-eicosyl amine, eicosyl triacontyl amine, trimethyl amine, triethyl amine, methyl ethyl propyl amine, dimethyl butyl amine, dodecyl dimethyl amine, octadecyl diethyl amine, hentriacontyl dibutyl amine, ethylenediamine, diethylenetriamine, triethylenetetramine, tetraethylenepentamine, pentaethylenehexamine, propylenediamine, dipropylenetriamine, tripropylenetetraamine, tetrapropylenepentamine, piperizine, piperidine, and the like.

An especially useful class of amines that can be color stabilized by the present invention are those amines having the structure:

wherein $R_1$ is an alkyl group containing about 6–30 carbon atoms, $R_2$ is an alkyl group containing about 1–30 carbon atoms and $R_3$ is hydrogen or an alkyl group containing about 1–30 carbon atoms.

Within this preferred class of aliphatic amines is a highly preferred subgenus of amines wherein $R_1$ is a substantially linear primary alkyl group and $R_2$ and $R_3$ are methyl groups. By substantially linear is meant that the alkyl chain has little if any side branching although it can contain a minor amount of short side branches such as methyl or ethyl branching. These amines include hexyl dimethyl amine, octyl dimethyl amine, decyl dimethyl amine, dodecyl dimethyl amine, tetradecyl dimethyl amine, hexadecyl dimethyl amine, octadecyl dimethyl amine, eicosyl dimethyl amine, docosyl dimethyl amine, triacontyl dimethyl amine and the like.

Another highly preferred subgenus of aliphatic amines are those amines having the above structure wherein $R_1$ and $R_2$ are substantially linear primary alkyl groups containing about 6–30 carbon atoms and $R_3$ is a methyl group. These include amines such as dihexyl methylamine, dioctyl methylamine, didecyl methylamine, didodecyl methylamine, ditetradecyl methylamine, dihexadecyl methylamine, dioctadecyl methylamine, dieicosyl methylamine, hexyl octyl methylamine, octyl dodecyl methylamine, dodecyl tetradecyl methylamine, dodecyl hexadecyl methylamine, tetradecyl hexadecyl methylamine, tetradecyl octadecyl methylamine, hexadecyl octadecyl methylamine, octadecyl eicosyl methylamine and the like. In this group it is still more preferred that $R_1$ and $R_2$ contain about 6–14 carbon atoms.

The additives that have been used successfully to inhibit color formation in the aliphatic amines are ethylenediamine tetraacetic acid, salts of ethylenediamine tetraacetic acid, nitrilotris methylenephosphonic acid, salts of nitrilotris methylenephosphonic acid, 8-hydroxy-quinoline and mixtures of any two or more of the foregoing additives.

The salts referred to include metal salts such as the alkali or alkaline earth metal salts such as the disodium salts of ethylenediamine tetraacetic acid (EDTA 2Na). The salt can also be formed from ammonia or other basic compounds including amines. Of course if the additive is added in its acid form, it can react with the amine substrate to form amine salts of the initial acidic additive. Excellent results have been achieved by the addition of the disodium salt of ethylenediamine tetraacetic acid.

The additives have little solubility in the aliphatic amines. This does not prevent them from achieving the desired results. The additives can be merely added to the amines in solid form and stirred so that good contact of the additives and the aliphatic amine is achieved. Alternatively, the amines can be passed through a bed of the additives such that intimate contact is achieved. Residual additives can be removed from the aliphatic amine prior to shipment or use by conventional methods such as by settling, filtration or both.

Only a small amount of additive is needed. Contact with as little as 50 parts per million parts of aliphatic amine (ppm) can give the desired result. A preferred range is about 100 to 10,000 ppm, more preferably 300-2,000 ppm and most preferably about 1000 ppm. Of course an excess amount of additive can be used but this is neither necessary nor economical as long as good contact is obtained between the additive and the entire bulk of the aliphatic amine.

Tests were conducted to demonstrate the effectiveness of various additives. In these tests a small amount of the test additive was slurried into the test amine (didecylmethylamine) in glass bottles. The bottles with loose caps were stored for 11 weeks and 2 days under ambient storage conditions. Storage was continued in an oven at 85°-90° for four more days. At this time color measurements were made using the APHA method. The initial APHA color rating of the amine prior to storage was 7.5. The color rating after the storage test is given in the following table:

TABLE I

| Additive | APHA Rating |
|---|---|
| none | 150 |
| EDTA—2Na[1] | 35 |

[1]Ethylenediamine tetraacetic acid di-sodium salt

A second test was conducted in a similar manner except that the bottles were stored uncapped for two days at 85°-90° C. The results of the storage tests are given in the following table:

TABLE II

| Additive | APHA Color Rating |
|---|---|
| None | 200 |
| NTP[1] (470 ppm) | 25 |
| EDTA—2Na[2] (165 ppm) | 125 |
| EDTA—2Na[2] (47 ppm) | 125 |
| EDTA[3] (212 ppm) | 125 |
| 8-Hydroxyquinoline | 70 |

[1]Nitrilotris methylenephosphonic acid
[2]Ethylenediamine tetraacetic acid di-sodium salt
[3]Ethylenediamine tetraacetic acid In another test samples of didecyl methylamine containing various additives were stored at 70° C. Results of this test use given in the following Table III.

TABLE III

| Additive | APHA Color Rating | |
|---|---|---|
| | 3 days | 6 Days |
| None | 65 | 100+ |
| EDTA—2Na (50 ppm) | 40 | 90 |
| EDTA—2Na (100 ppm) | 35-40 | 90 |
| EDTA—2Na (150 ppm) | 35 | 65 |
| EDTA—2Na (1000 ppm) | 25 | 35 |
| Sodium Acetate (100 ppm) | 80-90 | 100+ |
| Sodium Citrate (100 ppm) | 50 | 100+ |
| Ascorbic Acid (100 ppm) | 45 | 100+ |

A further test was carried out using octadecyl dimethylamine. The samples were stored at 70° C.

TABLE IV

| Additive | APHA Color Rating | | | |
|---|---|---|---|---|
| | 1 Day | 2 Days | 3 Days | 4 Days |
| None | 40 | 65 | 90 | 100+ |
| EDTA—2Na (50 ppm) | 10 | 25 | 35-40 | 45 |
| EDTA—2Na (100 ppm) | 10 | 20-25 | 30 | 40 |

TABLE IV-continued

| Additive | APHA Color Rating | | | |
|---|---|---|---|---|
| | 1 Day | 2 Days | 3 Days | 4 Days |
| EDTA—2Na (150 ppm) | 10 | 10 | 20-25 | 25-30 |

In the next storage test octadecyldimethylamine was stored in an oven at 85° C. The initial APHA color rating was 10. The color rating after storage for ten days is given in the following table:

TABLE V

| Additive | APHA Rating |
|---|---|
| none | 40, 70 |
| EDTA—2Na[1] (300 ppm) | 15 |

The results of the tests confirmed that the additives of the invention are effective in inhibiting the development of color in amines during storage.

I claim:

1. A color stabilized aliphatic amine composition wherein said amine has the formula:

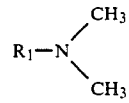

wherein $R_1$ is a primary alkyl group containing about 6-30 carbon atoms, said composition containing a color suppressing amount of an additive selected from the group consisting of nitrilotris methylenephosphonic acid, salts of nitrilotris methylenephosphonic acid and mixtures thereof.

2. A color stabilized aliphatic amine composition wherein said amine has the formula:

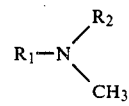

wherein $R_1$ and $R_2$ are primary alkyl groups containing about 6-30 carbon atoms, said composition containing a color suppressing amount of an additive selected from the group consisting of nitrilotris methylenephosphonic acid, salts of nitrilotris methylenephosphonic acid and mixtures thereof.

3. A method of preventing the formation of color in an aliphatic amine composition during storage wherein said aliphatic amines have the formula:

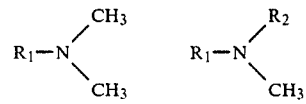

wherein $R_1$ and $R_2$ are primary alkyl groups containing about 6-30 carbon atoms, said method comprising contacting said amine with an effective amount of a compound selected from the group consisting of nitrilotris methylenephosphonic acid, salts of nitrilotris methylenephosphonic acid, and mixtures thereof before the formation of an objectionable color.

4. A composition of claim 1 wherein said additive is nitrilotris methylenephosphonic acid.

5. A composition of claim 2 wherein said additive is nitrilotris methylenephosphonic acid.

6. A method of claim 3 wherein said compound is nitrilotris methylenephosphonic acid.

* * * * *